United States Patent
Lee

(10) Patent No.: US 6,740,273 B2
(45) Date of Patent: May 25, 2004

(54) METHOD FOR MAKING BALLOON CATHETER

(76) Inventor: Keun-Ho Lee, #1388-1802 Greentown, 1185-Q Joang-dong, Wonmi-gu (KR)

( * ) Notice: Subject to any disclaimer, the term of this patent is extended or adjusted under 35 U.S.C. 154(b) by 42 days.

(21) Appl. No.: 09/995,450

(22) Filed: Nov. 27, 2001

(65) Prior Publication Data

US 2002/0084551 A1 Jul. 4, 2002

(30) Foreign Application Priority Data

Jan. 3, 2001 (KR) ........................................ 2001-000127
Jun. 23, 2001 (KR) ........................................ 2001-036004

(51) Int. Cl.$^7$ ............................ B29C 47/02; B29C 47/04
(52) U.S. Cl. ........................ 264/130; 264/150; 264/156; 264/159; 264/152; 264/250; 264/255; 264/271.1; 264/294
(58) Field of Search ................................ 264/156, 250, 264/255, 294, 271.1, 130, 150, 155, 159, 148, 149, 152, 171.12, 171.13

(56) References Cited

U.S. PATENT DOCUMENTS

| | | | | |
|---|---|---|---|---|
| 3,304,353 A | * | 2/1967 | Harautuneian | 264/515 |
| 3,544,668 A | * | 12/1970 | Dereniuk | 264/135 |
| 3,736,939 A | * | 6/1973 | Taylor | 604/265 |
| 3,865,666 A | * | 2/1975 | Shoney | 156/245 |
| 3,965,909 A | * | 6/1976 | Waddell et al. | 604/269 |
| 3,983,879 A | * | 10/1976 | Todd | 604/96.01 |
| 4,178,937 A | * | 12/1979 | Taylor et al. | 604/103 |
| 4,265,848 A | * | 5/1981 | Rusch | 264/130 |
| 4,447,228 A | * | 5/1984 | Patel | 604/103 |
| 5,137,671 A | * | 8/1992 | Conway et al. | 264/130 |
| 5,370,899 A | * | 12/1994 | Conway et al. | 427/2.3 |

* cited by examiner

*Primary Examiner*—Edmund H. Lee
(74) *Attorney, Agent, or Firm*—Lee, Hong, Degerman, Kang & Schmadeka

(57) ABSTRACT

The present invention relates to a method for making a silicon balloon catheter in which a first tube having its outer diameter slightly smaller than that of a desired catheter is formed by an extruding method, mold lubricant is coated at a portion of a balloon injection opening, a thin film type second tube is formed at the coated outer surface of the first tube by a second extruding, and then the catheter is vulcanized and cut. As a result, when liquid is injected to an expansion tube, the second tube is separated from the first tube, thereby performing a function as a balloon. The method for making a balloon catheter using silicon rubber includes the steps of: forming a first tube by extruding firstly, the tube having its outer diameter slightly smaller than that of a desired catheter, then vulcanizing and cutting the first tube; punching two balloon injection openings having small diameter at a portion for expanding into balloon in the first tube after inserting a support rod into a discharge tube path; coating mold lubricant at a portion of the balloon injection opening; connecting the first tubes coated the mold lubricant by using a connection unit after removing the support rod, and thereafter forming a second tube at the coated outside surface of the first tube by extruding secondly, performing a vulcanizing process and cutting again; forming a tip at the tip portion of the first and second tubes; and punching a urine discharge opening at the first tube.

5 Claims, 12 Drawing Sheets

METHOD FOR MAKING BALLOON CATHETER

BACKGROUND OF THE INVENTION

1. Field of the Invention

The present invention relates to a method for making a silicon balloon catheter, and more particularly to a method for making a silicon balloon catheter in which a balloon is formed on a lumen tube having a fluid drainage lumen and an inflation lumen so that it is inflated when a liquid is injected into the balloon though the inflation lumen.

2. Description of the Related Art

In general, a catheter made of silicon is a thin and long tube adapted to be inserted into the human body in order to draw blood or to inject medicine. Also, such a catheter may be used to drain urine. In this case, the catheter is inserted into the bladder through the urethra so as to drain urine collected in the bladder.

FIG. 1 is a sectional view illustrating a conventional balloon catheter. FIG. 2 is a flow chart illustrating a conventional method for manufacturing the balloon catheter.

As shown in FIG. 1, the conventional balloon catheter includes a lumen tube 13 formed with a partition 19 therein to define a primary lumen 12 and an inflation lumen 14, and a balloon layer 16 partially bonded to an outer surface of the lumen tube 13 to provide a balloon. The primary lumen 12 serves to drain urine induced from the bladder through a urine drainage hole 17, whereas the inflation lumen 14 serves to inflate the balloon provided by the balloon layer 16. An inflation hole 15 is also formed at the lumen tube 13 in order to communicate the inflation lumen 14 with the interior of the balloon.

In order to manufacture the balloon catheter having the above mentioned configuration, an extrusion process is carried out to extrude an intermediate tube having the primary lumen 12 and inflation lumen 14 (Step S1), as shown in FIG. 2. Thereafter, the extruded intermediate tube is vulcanized (Step S2), and then cut into tube pieces having a desired length, that is, lumen tubes 13 (Step S3).

Subsequently, the inflation hole 15 and urine drainage hole 17 are perforated through each lumen tube 13 (Step S4). A tip 11 is then formed at one end of each lumen tube 13 (Step S5). Thereafter, a balloon manufactured in a separate molding process (Step S6) is bonded, as the balloon layer 16, to the outer surface of each lumen tube 13 by an adhesive (Step S7). Each lumen tube 13 is then subjected to an overcoating process (Step S8) to complete the balloon catheter having the configuration of FIG. 1.

In the above mentioned conventional balloon catheter, however, there is a problem in that it may cause a patient great pain during a surgical operation because its balloon-bonded portion has a diameter relatively larger than that of other portions, Furthermore, the bonded portions of the balloon maybe separated.

Another conventional catheter manufacturing method is disclosed in U.S. Pat. No. 5,137,671.

This method will be described hereinafter with reference to FIGS. 3a to 3g. First, a double lumen tube 100 is prepared, as shown in FIG. 3a The double lumen tube 100 is formed with a first lumen 120 (a larger fluid conduit lumen) and a second lumen 140 (a smaller capillary lumen).

A capillary lumen access opening 160 is punched through at an intermediate portion of the prepared lumen tube 100, that is, a balloon inflating portion, so that it communicates with the second lumen 140, as shown in FIG. 3b. The second lumen 140 is then filled with a polymeric fill material 180 such as silicon rubber between one end thereof (that is, the left end in FIG. 3b)and a point just before the capillary lumen access opening 160. A tip 200 is attached to one end of the lumen tube 100 corresponding to the one end of the second lumen 140, so that both of the fast and second lumens 120 and 140 are closed at one end thereof.

Subsequently, a portion of the lumen tube 100 extending from one end of the lumen tube 100 to the balloon inflating portion, that is, up to the line A—A in FIG. 3c, is dipped into a bond preventing agent solution (a liquid soap or petrolatum), and then dried, so that it is coated with a solidified bond preventing agent layer 300. The bond preventing agent layer 300 fills the capillary lumen access opening 160 and a portion of the second lumen 140. Thus, the bond preventing agent layer 300 has a cross section as shown in FIG. 3c. That is, the portion of the second lumen 140 between the line A—A and the capillary lumen access opening 160 is filled with the bond preventing agent layer 300, whereas the outer surface portion of the lumen tube 100 between the line A—A and the end of the lumen tube 100 adjacent to the tip 200 is coated with the bond preventing agent layer 300, along with the tip 200.

Thereafter, a portion of the lumen tube 100 extending up to the line B—B in FIG. 3c, that is, just before the balloon inflating portion, is treated using a surface active agent, and then dipped into hot, water or other hot aqueous solution several times, so as to remove the bond preventing agent layer 300 therefrom. Thus, the bond preventing agent layer 300 remains only at the balloon inflating portion of the lumen tube 100, as shown in FIG. 3d. An overcoat layer 400 is then coated over the entire outer surface of the lumen tube 100, as shown in FIG. 3e. The overcoat layer 400 may have a multi-layer structure including laminated layers 410 and 420.

The remaining bond preventing agent layer 300 filling and covering the balloon inflating portion is completely removed through the second lumen 140 of the lumen tube 100, thereby forming a balloon cavity 440, as shown in FIG. 3f. Thus, a balloon catheter is obtained. Referring to FIG. 3g, it can be seen that the conventional lumen tube 20 has a cross-sectional shape where its thickness ta and thickness Ta are relatively large. Typically, the conventional lumen tube 13 has a minimum thickness between the outer surface thereof and the surface of the inflation lumen 14, that is, ta, corresponding to 0.5 mm, while having a minimum thickness between the outer surface thereof and the surface of the fluid drainage lumen 12, that is, Ta, corresponding to 0.9 mm.

Accordingly, workability in a subsequent operation for perforating inflation apertures while allowing the fluid drainage lumen to have a size as large as possible is significantly reduced.

This balloon catheter manufacturing method has a problem in that it causes environmental pollution due to waste water produced during the procedure of dipping the lumen tube 100 into water several times in order to remove the bond preventing agent from the portion of the lumen tube 100 (between the line B—B and the tip-side end) other than the balloon inflating portion.

Additionally, where the bond preventing agent is incompletely removed, the residue thereof is moved to the peripheral edge of the balloon cavity formed at the balloon inflating portion when the balloon cavity is inflated, thereby causing the overcoat layer to be stripped around the balloon inflating portion. As a result, the overcoat layer may be inflated around the balloon inflating portion.

Also, the above mentioned conventional balloon catheter manufacturing method still has the problem caused by the diameter of the balloon inflating portion being larger than that of other portions As another conventional example, there is a silicon rubber catheter disclosed in Japanese Patent No. 3015310 registered on Jun. 21, 1995.

In this catheter, a balloon is formed on the outer surface of a catheter body such that it is integral with the catheter body. The catheter body is formed using silicon rubber in accordance with a primary extrusion process so that it is defined with a fluid conduit lumen and a capillary lumen therein, and formed with a channel at the outer surface thereof The catheter body is subjected to a vulcanization process, and then coated with a bond preventing agent at a balloon forming portion thereof Thereafter, a balloon layer is laminated using silicon rubber over the outer surface of the catheter body in accordance with a secondary extrusion process, and then vulcanized. A tip is then formed at the catheter body. In this structure, the outer surface of the balloon layer is flush with the outer surface of the catheter body at the catheter body portion other than the balloon forming portion, so that there is no step formed at the outer surface of the catheter body. Accordingly, there is no resistance caused by steps.

However, it is difficult to practically manufacture such a catheter, in which the balloon is integral with the catheter body.

This is because the silicon rubber layer coated in the secondary extrusion process may penetrate into the channel. Where the silicon rubber layer is coated without any penetration thereof into the channel, it is difficult to obtain a sufficient bonding force to the catheter body. In this case, the silicon rubber layer may be stripped even at a region other than the balloon forming portion.

SUMMARY OF THE INVENTION

Accordingly, the present invention is directed to a silicon rubber balloon catheter that solves the above problems.

An object of the present invention is to not require a step at a balloon portion thereof, thereby being capable of alleviating pain caused to a patient during a surgical operation while preventing a balloon layer from being separated from a region other than the balloon portion.

It is another object of the present invention to achieve an improvement in productivity and a reduction in manufacturing costs.

Additional features and advantages of the invention will be set forth in the description which follows, and in part will be apparent from the description, or may be learned by practice of the invention. The objectives and other advantages of the invention will be realize and attained by the structure particularly pointed out in the written description and claims hereof as well as the appended drawings.

To achieve these and other advantages and in accordance with the purpose of the present invention, as embodied and broadly described, a method for making a silicon rubber balloon catheter, the method comprising the steps of extruding an elongated lumen tube provided with a drainage lumen and an inflation lumen therein, wherein the elongated lumen tube has a diameter less than the silicon rubber balloon catheter; vulcanizing the elongated lumen tube; cutting the vulcanized elongated lumen tube to form one or more unit length lumen tubes; fitting a support rod in the drainage lumen of the unit length lumen tube; forming two apertures through the unit length lumen tube at the a balloon forming region, wherein the two apertures each have a diameter of approximately 0.5 mm; coating an outer surface of the unit length lumen tube uniformly at the balloon forming region with a bond preventing agent while turning the unit length lumen tube along its circumference, wherein the coating of the bond preventing agent has straight edges; removing the support rod from the unit length lumen tube; connecting the coated unit length lumen tube to another coated unit length lumen tube with a connector to form a series of unit length lumen tubes; extruding a balloon tube having uniform thickness over the series of unit length lumen tubes such that the series of unit length lumen tubes is within the balloon tube; ensuring that the bond preventing agent is not discolored or has not deteriorated; vulcanizing the balloon tube; cutting the balloon tube to form one or more unit length balloon tubes, wherein the unit length balloon tube is approximately equivalent in length to the unit length lumen tube; removing the connector from the unit length lumen tube; forming a tip at one end of the unit length balloon tube; and forming a urine drainage hole through the unit length balloon tube and through the drainage lumen within the unit length lumen tube.

It is to be understood that both the foregoing general description and the following detailed description are exemplary and explanatory and are intended to provide a further explanation of the invention as claimed.

BRIEF DESCRIPTION OF THE DRAWINGS

The above objects, and other features and advantages of the present invention will become more apparent after a reading of the following detailed description when taken in conjunction with the drawings, in which.

DESCRIPTION OF THE PREFERRED EMBODIMENTS

Preferred embodiments of the present invention will now be described in detail with reference to FIGS. 4a to 6.

Figure 5:
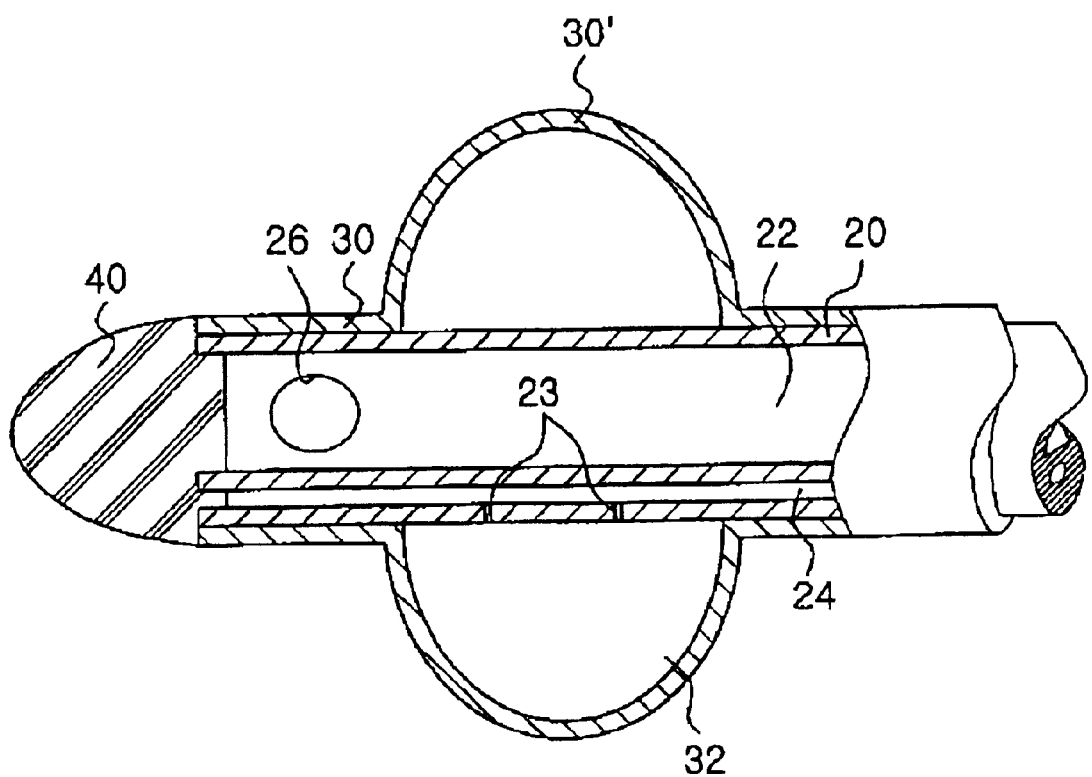
FIG. 5 is a sectional view illustrating the configuration of the balloon catheter manufactured in accordance with the method of the present invention.
Figure 6:
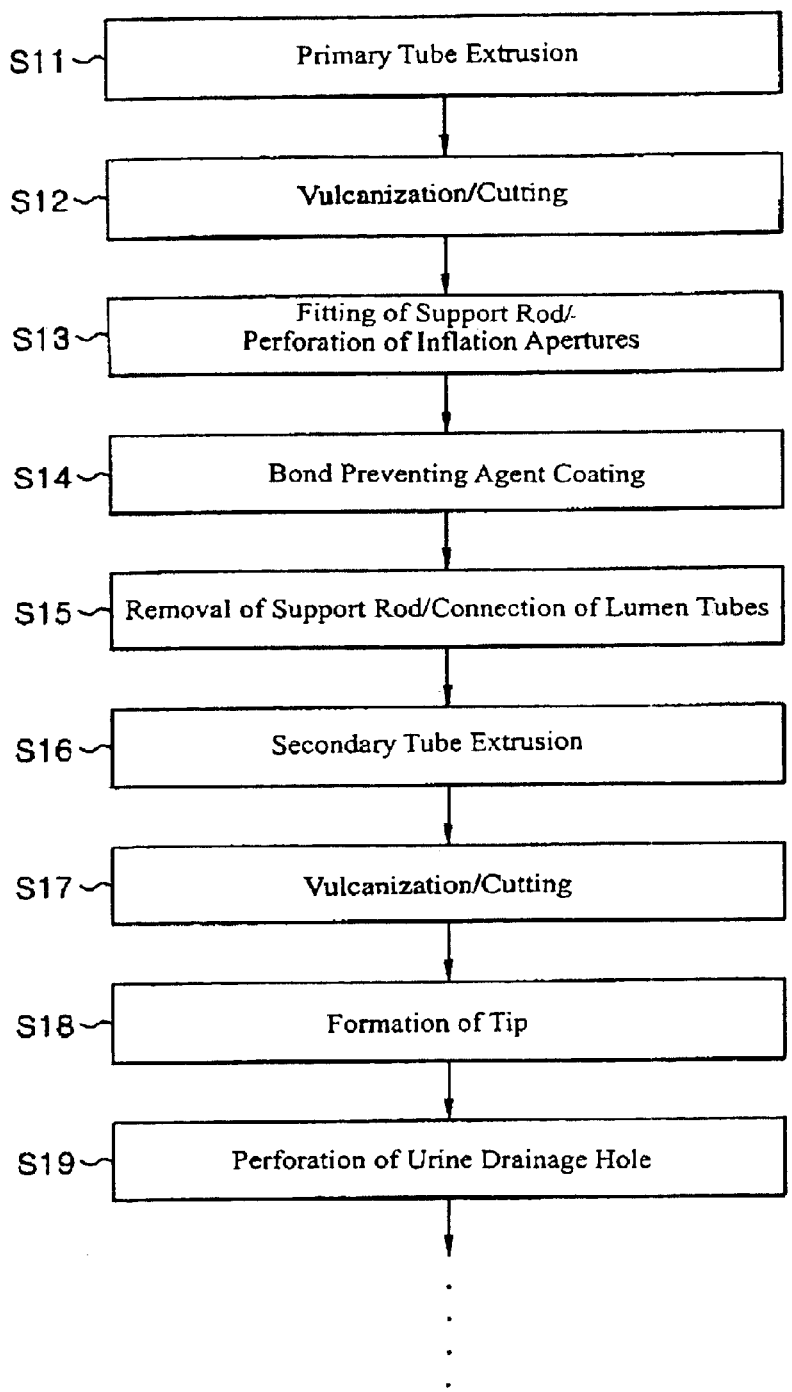
FIG. 6 is a flow chart illustrating the balloon catheter manufacturing method of the present invention.

FIGS. 4a to 4h are sectional views respectively illustrating sequential steps of a method for making a balloon catheter according to an embodiment of the present invention. FIG. 5 is a sectional view illustrating the configuration of the balloon catheter manufactured in accordance with the method of the present invention. FIG. 6 is a flow chart illustrating the balloon catheter manufacturing method of the present invention.

Figure 1:
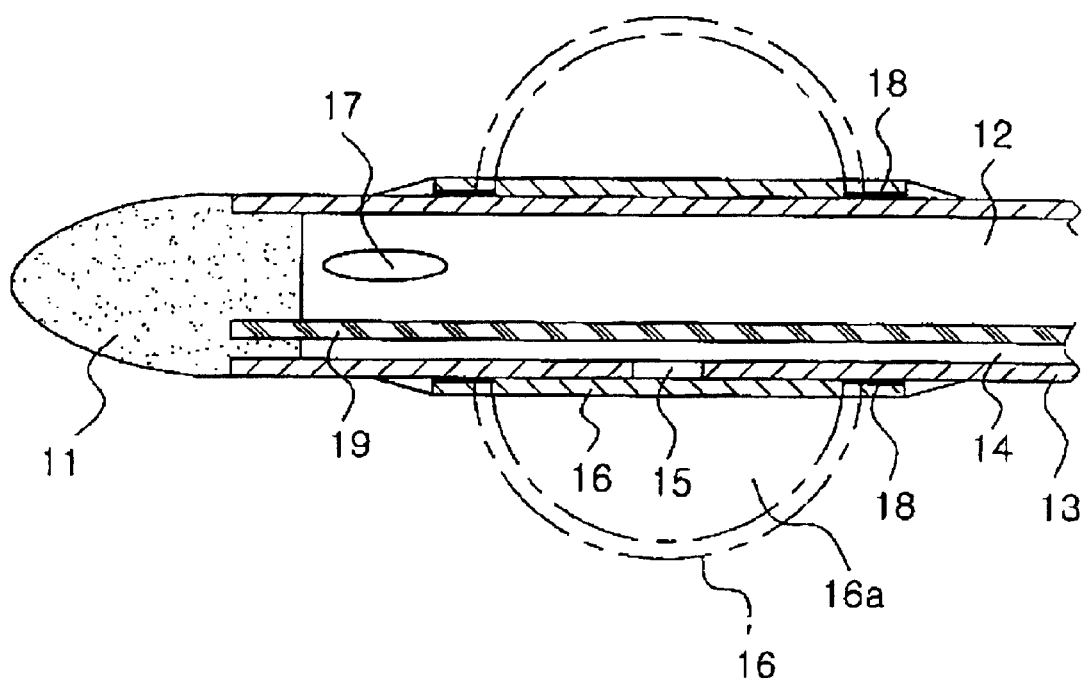
FIG. 1 is a sectional view illustrating a conventional balloon catheter.
Figure 2:
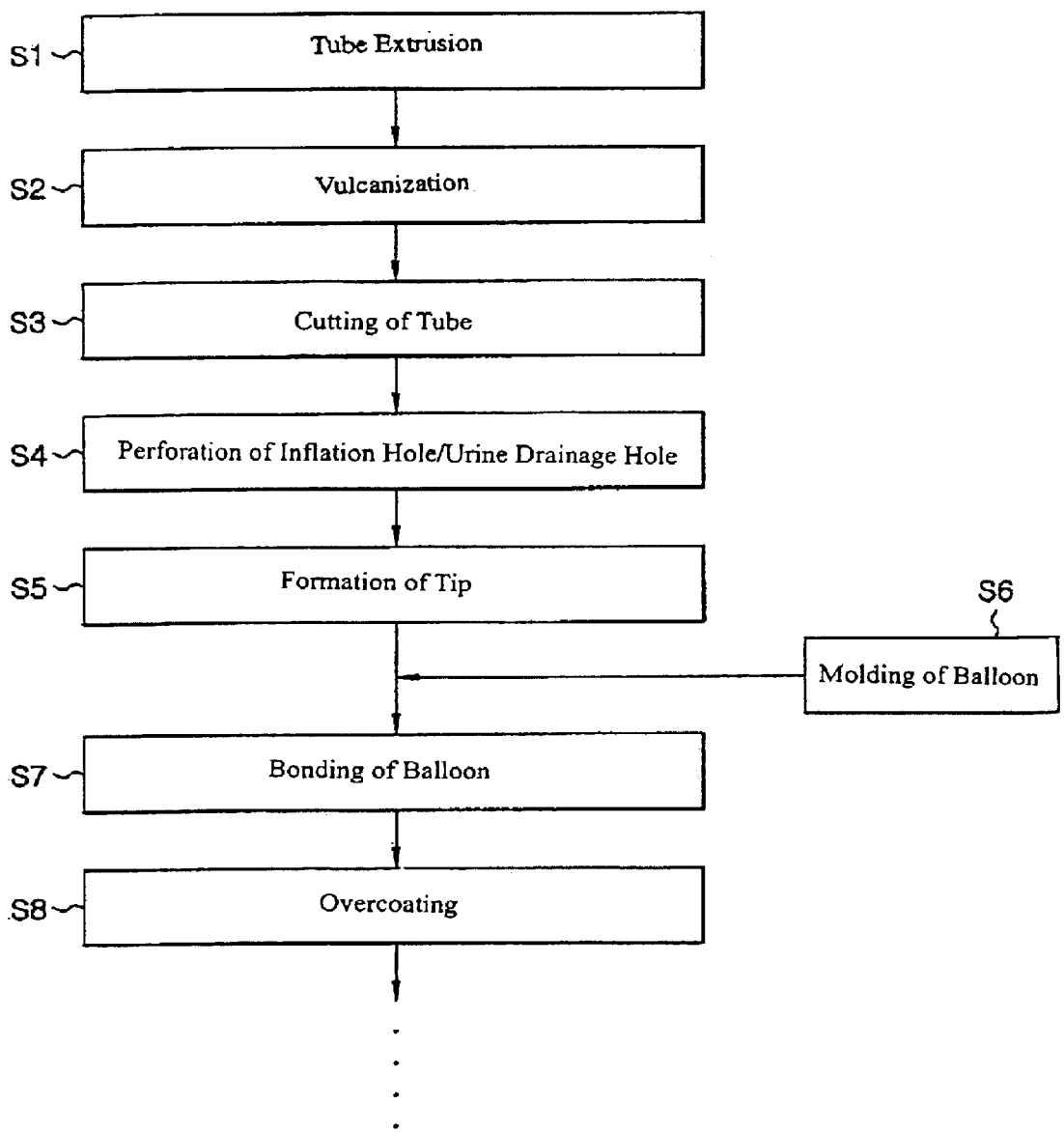
FIG. 2 is a flow chart illustrating a conventional method for manufacturing the balloon catheter.
Figure 3A:
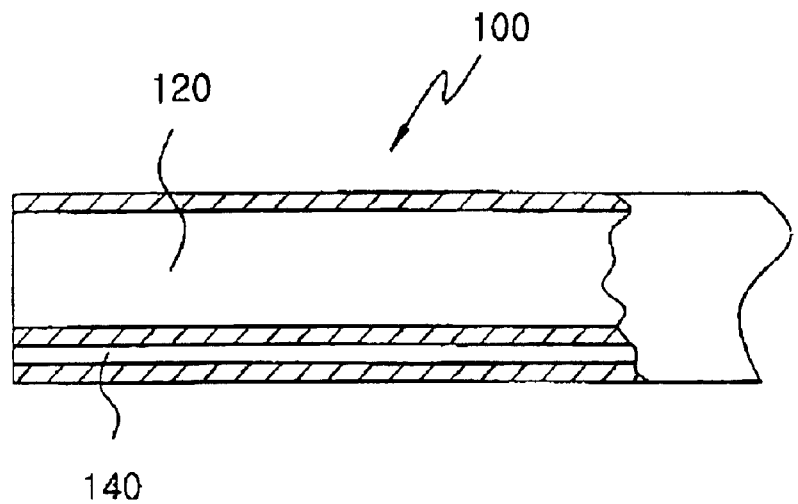
FIGS. 3a to 3g are sectional views respectively illustrating sequential steps of a conventional method for manufacturing a balloon catheter.
Figure 3B:
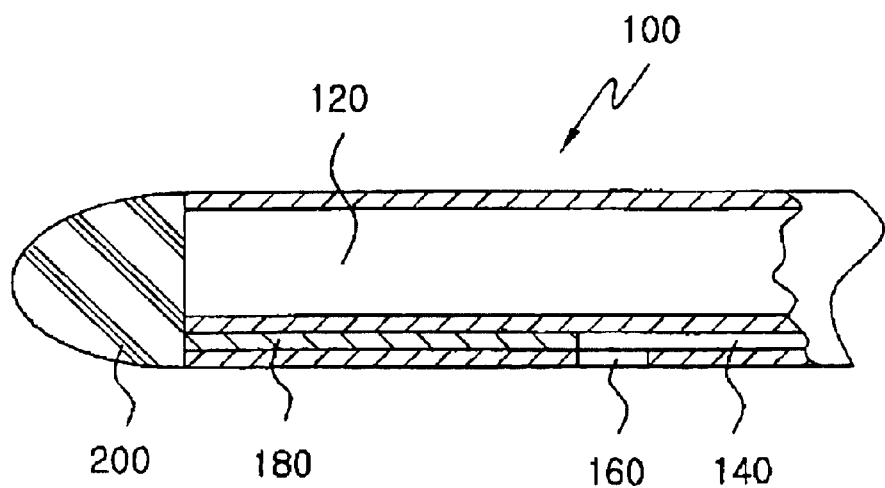
Figure 3C:
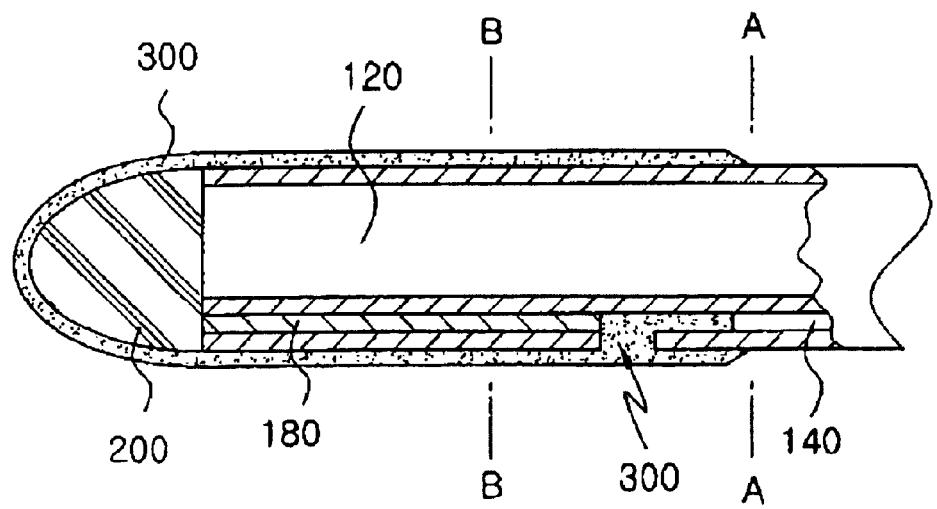
Figure 3D:
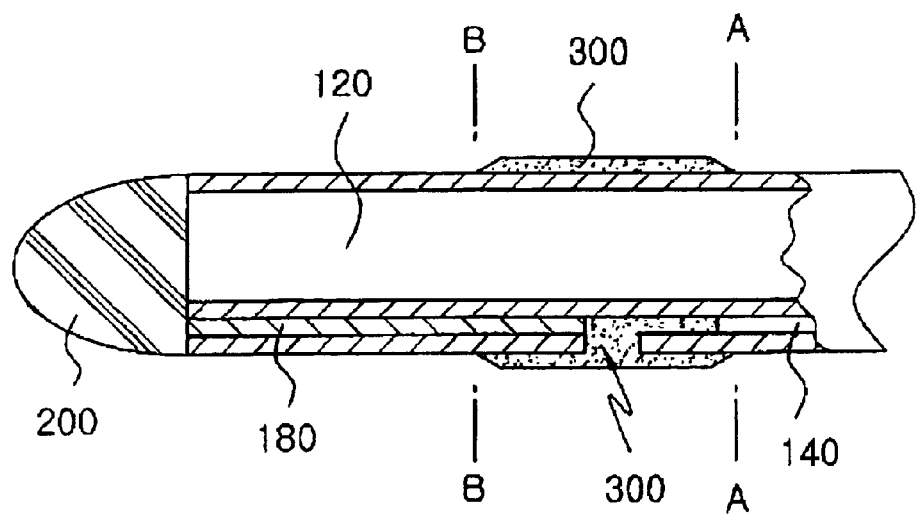
Figure 3E:
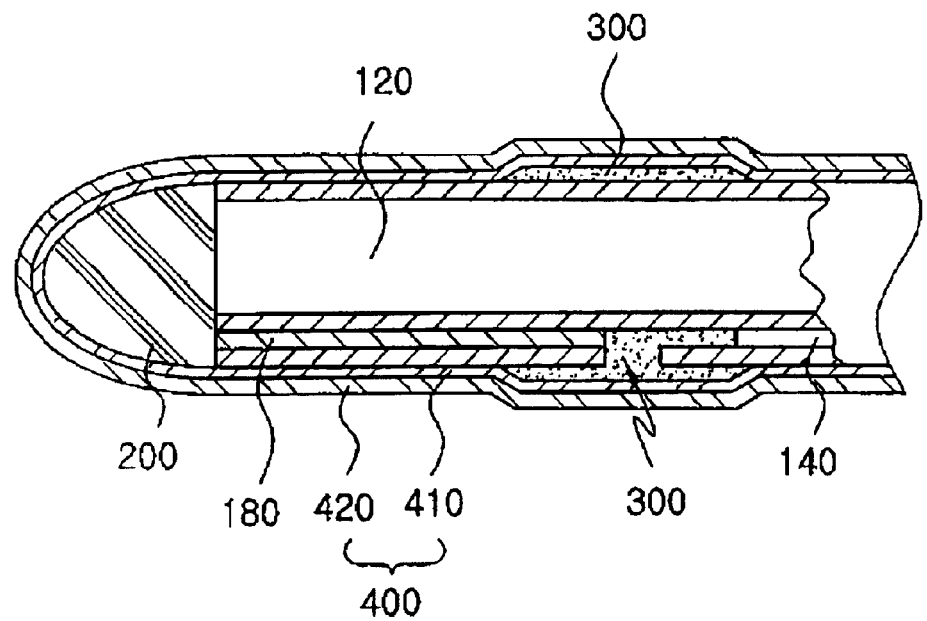
Figure 3F:
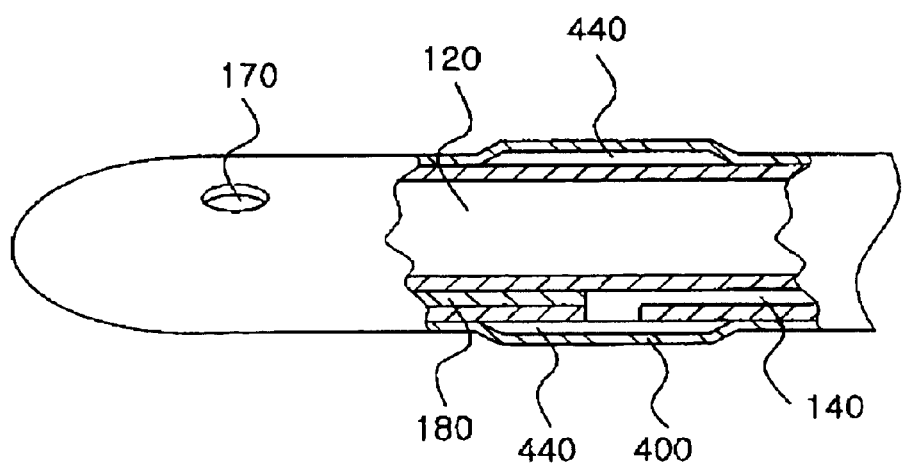
Figure 3G:
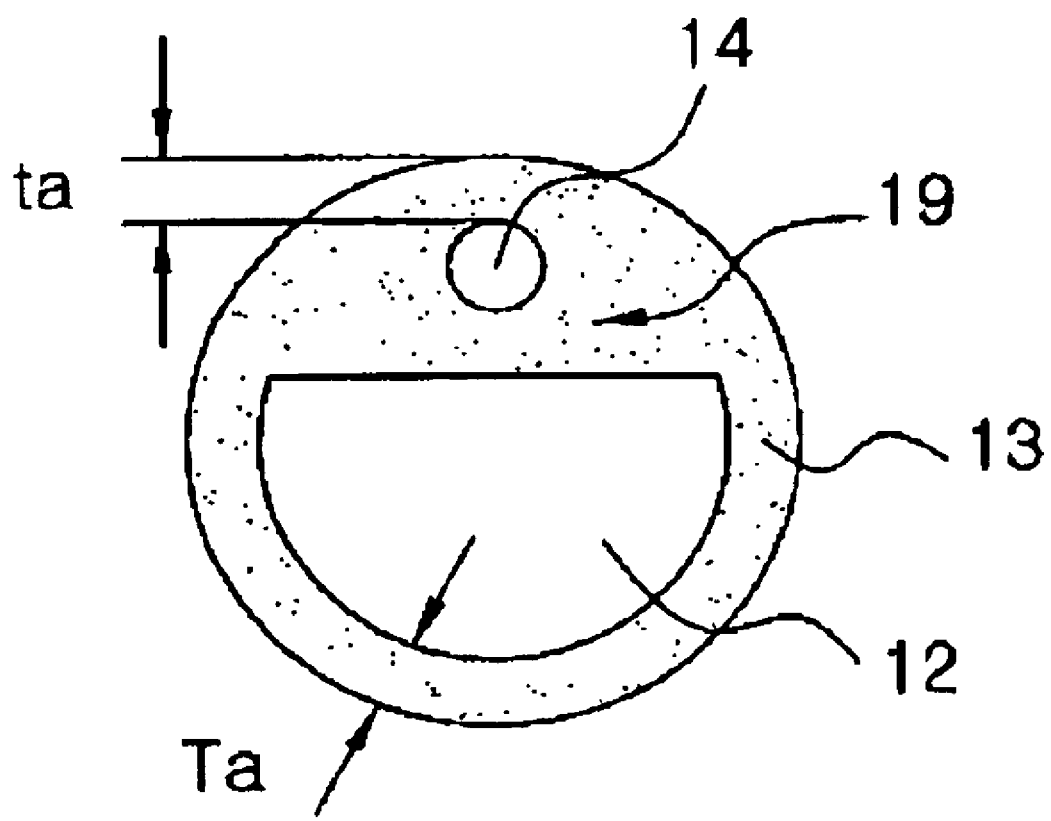
Figure 4A:
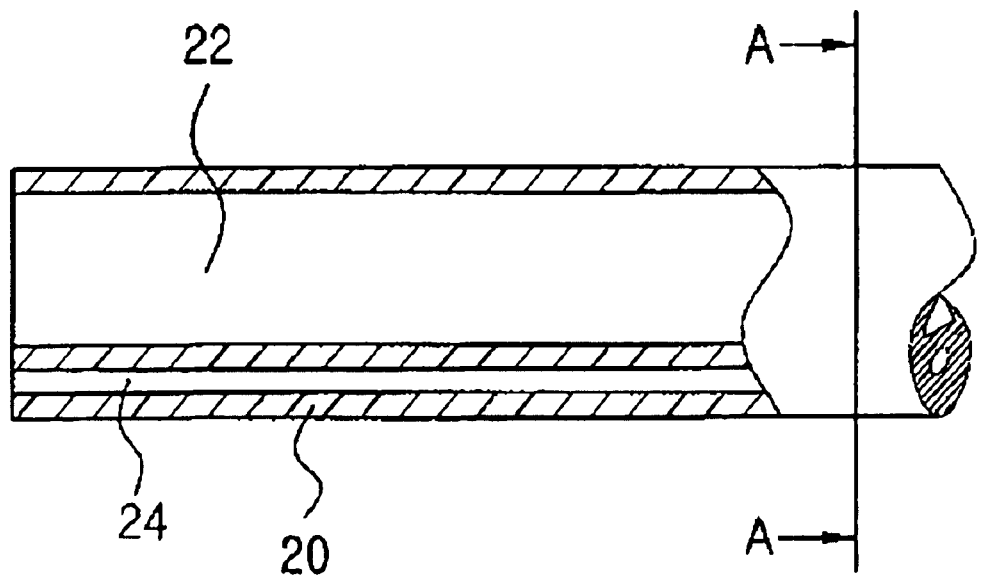
FIGS. 4a to 4h are sectional views respectively illustrating sequential steps of a method for making a balloon catheter according to an embodiment of the present invention.

In accordance with the illustrated preferred embodiment of the present invention, as shown in FIG. 4a, a lumen tube 20 is extruded in accordance with a primary extrusion process (Step S11 in FIG. 6). The lumen tube 20 is formed with a fluid drainage lumen 22 and an inflation lumen 24 while having an outer diameter slightly smaller than the outer diameter of a desired balloon catheter to be finally obtained. The extruded lumen tube 20 is then subjected to a vulcanization process so that it has a desired elasticity. In order to manufacture such a lumen tube in a continuous manner, an elongated lumen tube is practically extruded, which is, in turn, cut into a plurality of unit lumen tubes each corresponding to the lumen tube 20 (Step S12 in FIG. 6).

Figure 4B:
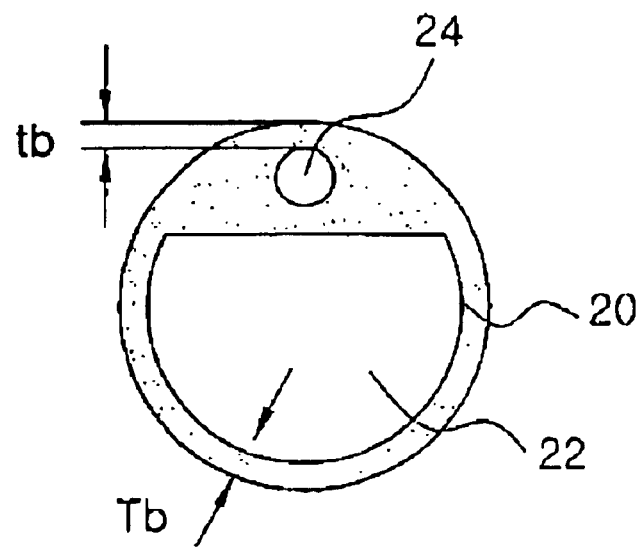

The lumen tube 20 has a cross-sectional shape shown in FIG. 4b. Thickness tb and thickness Tb, which are relatively small, illustrate an enhanced workability in a subsequent operation for perforating inflation apertures while making the fluid drainage lumen have a size as large as possible. This will be described in detail hereinafter.

Taking into consideration the thickness of an overcoat layer to be formed on the lumen tube 20 in a secondary extrusion process, the lumen tube 20 can have a reduced thickness, as described above and shown in FIG. 4b. The lumen tube 20 may have a minimum thickness between the outer surface thereof and the surface of the inflation lumen 24, that is, tb, corresponding to 0.3 mm, while having a minimum thickness between the outer surface thereof and the surface of the fluid drainage lumen 22, that is, Ta, corresponding to 0.7 mm.

In the method of the present invention, it is desirable to use a vertical extruder and a vertical vulcanizer in the primary extrusion process (Step S11) and the vulcanization process (Step S12) in the method of the present invention, respectively. Where the horizontal extruder and vulcanize are used, contact traces are formed. Even if these contact ties are fine, they remain in the form of defects at a region where a balloon is formed. The defects cause an eccentric inflation of the balloon or rupture of the balloon upon the inflation.

Figure 4C:
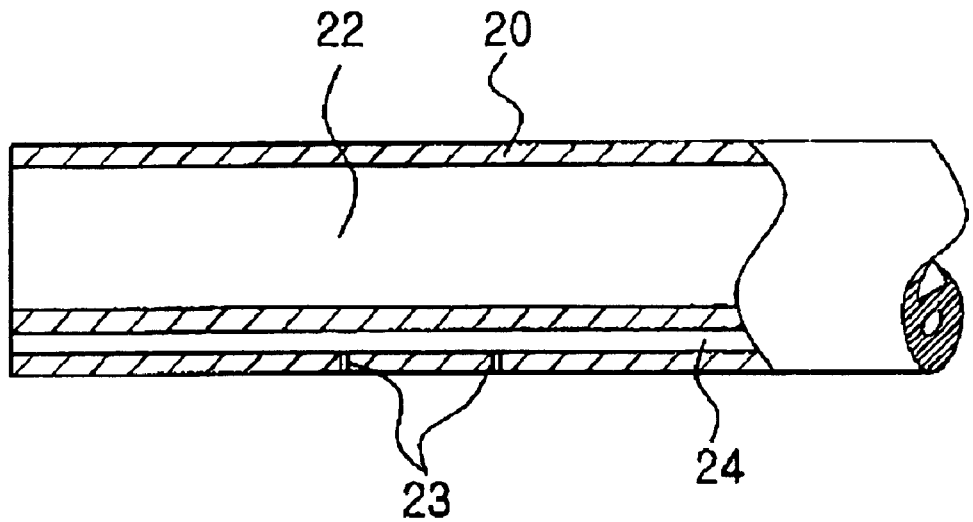
Figure 4D:
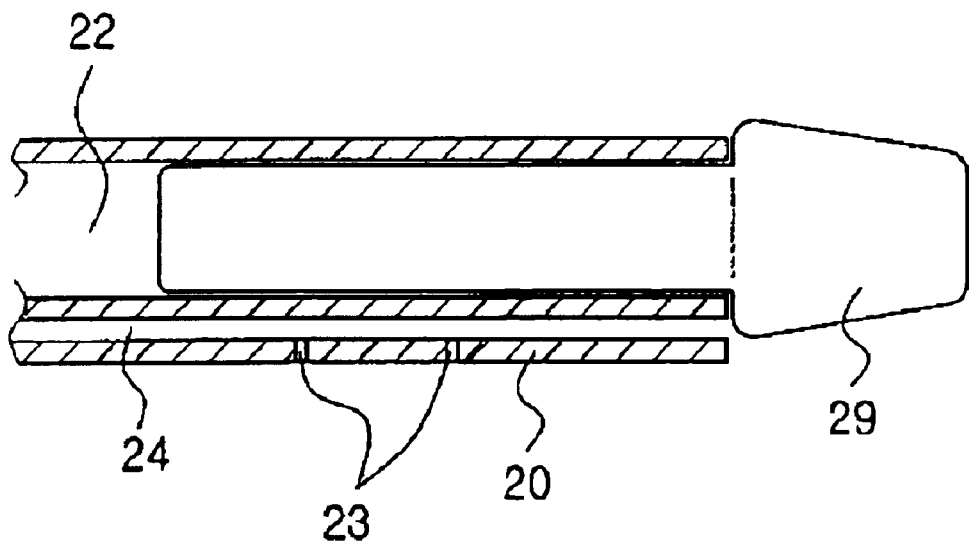

Thereafter, inflation apertures 23 are perforated through the lumen tube 20, as shown in FIG. 4c (Step S13). The perforating process can be conveniently carried out by inserting a support rod 29 into the fluid drainage lumen 22, thereby maintaining the lumen tube 20 in a straight state, as shown in FIG. 4d. Two inflation apertures 23 having a diameter (about 0.5 mm) smaller than that of the conventional inflation hole are formed at positions adjacent to opposite edges of the balloon region while being spaced apart from the opposite edges by a distance of about 2 to 3 mm, respectively.

Should the inflation apertures 23 be excessively large, a balloon layer subsequently coated to form a balloon in a secondary extrusion process (Step S16 in FIG. 6) may penetrate into the inflation apertures 23, thereby causing the balloon to have a non-uniform thickness. As a result the balloon may be ruptured upon its inflation.

Figure 4E:
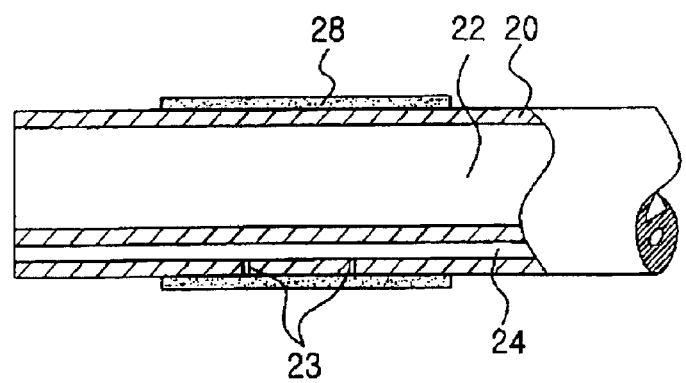

Thereafter, a bonding preventing agent 28 must be coated on the outer surface of the lumen tube 20 at a region only where the inflation apertures 23 are formed, as shown in FIG. 4e (Step S14). In this coating process, care should be taken because the bonding preventing agent 28 must be uniformly and completely coated around the outer surface of the lumen tube 20 at the balloon forming region, where the inflation aperture 23 are formed, such that its edges extend straight.

For the bonding preventing agent 28, a commercially available liquid soap or a mixture of an aqueous transparent ink with a Teflon solution may be used. In order to obtain a desired viscosity, the bonding preventing agent 28 may be added with water or alcohol.

The coating process is carried out by wetting a sponge with the bonding preventing agent 28 having an appropriate viscosity obtained in the above described manner, bringing the sponge into contact with a portion of the lumen tube 20 compounding to the balloon forming region, and rotating the lumen tube 20 one turn in a state of being in contact with the sponge. Thus, the bonding preventing agent 28 can be uniformly coated over the lumen tube portion corresponding to the balloon forming region. The coated bonding preventing agent 28 is then dried by warm air of about 60 to 70° C. gently blown thereto (Step S14).

Figure 4F:
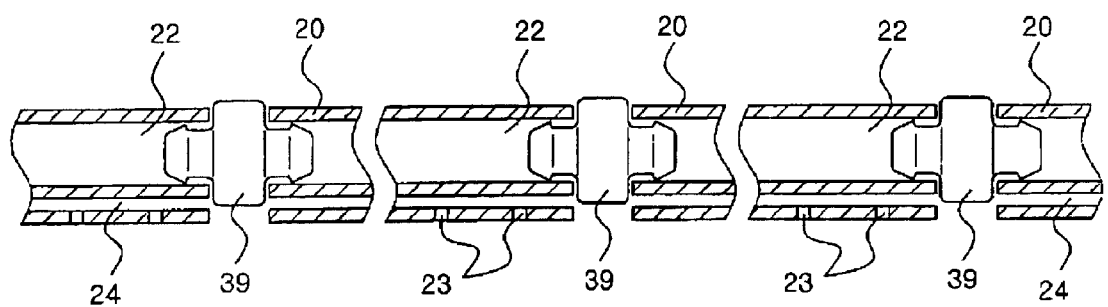

After the bonding preventing agent 28 is sufficiently dried, the support rod 29 is removed from the fluid drainage lumen 22 of the lumen tube 20 (FIG. 4e). As shown in FIG. 4f, the lumen tube 20 is then fitted around one end of a connector 39 so that it is connected with another lumen tube 20 fitted around the other end of the connector 39. In such a manner, a plurality of lumen tubes 20 are connected in series by a plurality of connectors 39 (Step S15), so that a continuous secondary extrusion process can be carried out for the lumen tubes 20.

Figure 4G:
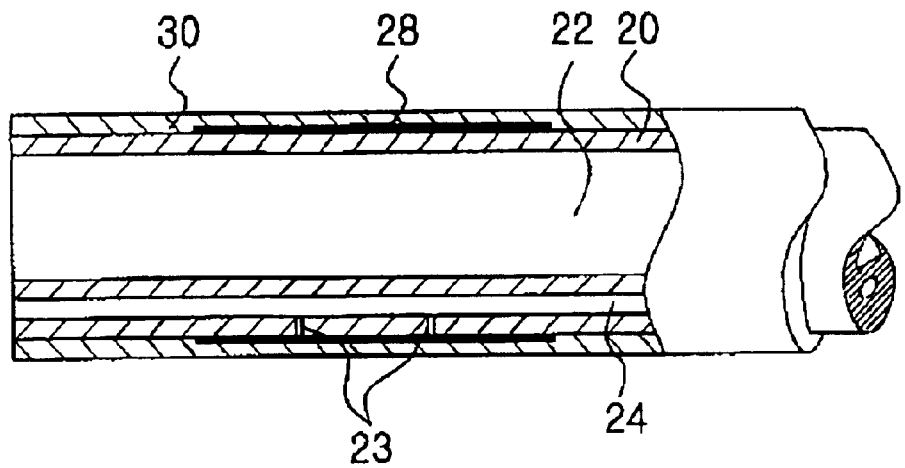

A thin silicon rubber tube is then extruded in accordance with the secondary extrusion process while passing the connected lumen tubes 20 through a vertical extruder and a vertical vulcanizer (Step S16), and then vulcanized (Step S17), so that a balloon tube 30 is coated over each lumen tube 20, as shown in FIG. 4g. The secondary extrusion process should be carefully carried out in order to obtain a uniform thickness of the balloon tube 30, which must be maintained, and to prevent discoloration and degradation in removability at the region where the bond preventing agent is coated.

Figure 4H:
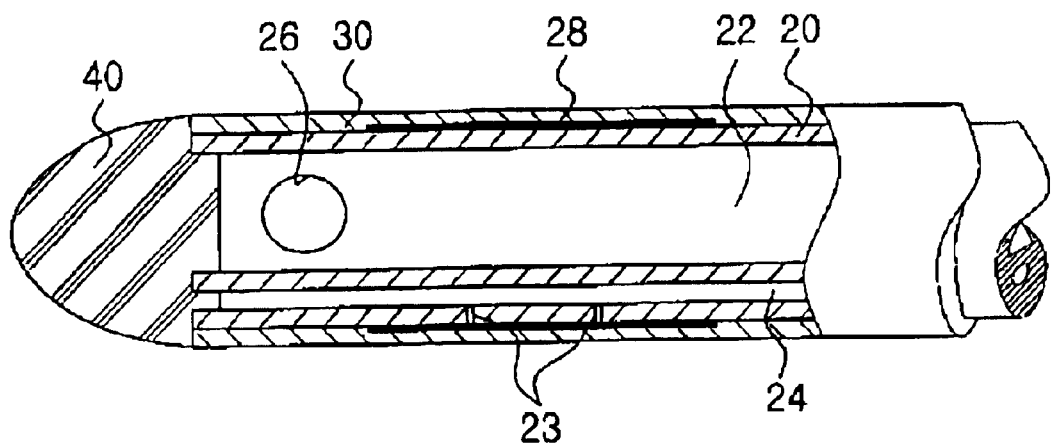

The vulcanized tube product is then cut into tube pieces respectively corresponding to the connected lumen tubes 20 at step S17. Subsequently, the connectors 39 are separated from the tube pieces, thereby separating the tube pieces. A tip 40 is then formed at one end of each tube piece, as shown in FIG. 4h (Step S18). Finally, a urine drainage hole 26 is perforated through each tube piece. Thus, balloon catheters are completely manufactured.

A balloon catheter manufactured in accordance with the above described procedures is shown in FIG. 5. In FIG. 5, the reference numeral 30 is a balloon portion of the balloon catheter provided by the balloon tube 30. When a liquid is injected into the balloon catheter through the inflation lumen 24, the balloon portion of the balloon catheter is symmetrically inflated.

In accordance with the present invention, it is possible to achieve a reduction in labor, and thus, a reduction in manufacturing costs because the manufacturing processes can be easily carried out, and the number of manufacturing processes is reduced.

As apparent from the above description, the present invention provides a method for making a balloon catheter having no step at its outer surface by primarily extruding a lumen tube having an outer diameter slightly smaller than that of a balloon catheter to be finally manufacture and coating a bond preventing agent on a portion of the lumen tube where a balloon is to be, formed, and secondarily extruding a tin balloon tube on the lumen tube. When a liquid is injected into the balloon catheters through an inflation lumen provided at the lumen tube, the balloon tube is inflated while being separated from the lumen tube at a region where the bond preventing agent is coated, so that it serves as a balloon. Since the balloon catheter has a uniform outer diameter without having any step at the outer surface thereof, it is possible to reduce the pain caused to a patient during a surgical operation. It is also possible to achieve a reduction in manufacturing costs through an increase in productivity while considerably reducing problems involved with the conventional cases, for example, separation of the balloon layer at a region other than the balloon region.

What is claimed is:

1. A method for making a silicon rubber balloon catheter, the method comprising the steps of:

extruding an elongated lumen tube provided with a drainage lumen and an inflation lumen therein, wherein the elongated lumen tube has a diameter less than the silicon rubber balloon catheter;

vulcanizing, the elongated lumen tube;

cutting the vulcanized elongated lumen tube to form one or more unit length lumen tubes;

fitting a support rod in the drainage lumen of the unit length lumen tube;

forming two apertures through the unit length lumen tube at a balloon forming region, wherein the two apertures each have a diameter of approximately 0.5 mm;

coating an outer surface of the unit length lumen tube uniformly at the balloon forming region with a bond preventing agent while turning the unit length lumen tube along its circumference, wherein the coating of the bond preventing agent has straight edges;

removing the support rod from the unit length lumen tube;

connecting the coated unit length lumen tube to another coated unit length lumen tube with a connector to form a series of unit length lumen tubes;

extruding a balloon tube having uniform thickness over the series of unit length lumen tubes such that the series of unit length lumen tubes is with in the balloon tube;

ensuring that the bond preventing agent is not discolored or has not deteriorated;

vulcanizing the balloon tube;

cutting the balloon tube to form one or more unit length balloon tubes, wherein the unit length balloon tube is approximately equivalent in length to the unit length lumen tube;

removing the connector from the unit length lumen tube;

forming a tip at one end of the unit length balloon tube; and forming a urine drainage hole through the unit length balloon tube and through the drainage lumen within the unit length lumen tube.

2. The method of claim 1, wherein the drainage lumen has a greater diameter than of the inflation lumen.

3. The method of claim 1, wherein the two apertures are formed through the unit length lumen tube at positions adjacent to opposite edges of the balloon forming region.

4. The method of claim 1, wherein the drainage hole is formed through the unit length balloon tube between the tip and the balloon forming region.

5. The method of claim 1, wherein the support rod is fitted in the drainage lumen of the unit length lumen tube to extend up to the balloon forming region.

* * * * *